US00PP19414P2

(12) United States Plant Patent
Snijder

(10) Patent No.: US PP19,414 P2
(45) Date of Patent: Nov. 4, 2008

(54) ***GERANIUM* PLANT NAMED 'FISUM LILAC EYE'**

(50) Latin Name: *Pelargonium×hortorum*
Varietal Denomination: Fisum Lilac Eye

(75) Inventor: Ronald Christiann Snijder, De Lier (NL)

(73) Assignee: Fides B.V., De Lier (NL)

( * ) Notice: Subject to any disclaimer, the term of this patent is extended or adjusted under 35 U.S.C. 154(b) by 152 days.

(21) Appl. No.: 11/633,118

(22) Filed: Dec. 1, 2006

(51) Int. Cl.
*A01H 5/00* (2006.01)

(52) U.S. Cl. ..... Plt./329

(58) Field of Classification Search ..... Plt./329, Plt./330, 324, 325
See application file for complete search history.

*Primary Examiner*—Howard J Locker
(74) *Attorney, Agent, or Firm*—C. A. Whealy

(57) ABSTRACT

A new and distinct cultivar of Zonal *Geranium* plant named 'Fisum Lilac Eye', characterized by its upright plant habit; freely basal branching habit; dark green-colored leaves; freely flowering habit; large semi-double red purple-colored flowers with slightly lighter-colored central splotches; and good garden performance.

1 Drawing Sheet

Botanical designation: *Pelargonium×hortorum*.
Cultivar denomination: 'Fisum Lilac Eye'.

BACKGROUND OF THE INVENTION

The present invention relates to a new and distinct cultivar of Zonal *Geranium*, botanically known as *Pelargonium× hortorum,* and hereinafter referred to by the name 'Fisum Lilac Eye'.

The new Zonal *Geranium* is a product of a planned breeding program conducted by the Inventor in De Lier, The Netherlands. The objective of the breeding program is to create new freely-branching and freely-flowering Zonal *Geranium* cultivars with attractive foliage and flower coloration.

The new Zonal *Geranium* originated from a cross-pollination made by the Inventor in De Lier, The Netherlands of two unnamed selections of *Pelargonium×hortorum,* not patented, in August, 2003. The cultivar Fisum Lilac Eye was discovered and selected by the Inventor as a flowering plant from within the progeny of the stated cross-pollination in a controlled environment in De Lier, The Netherlands, in March, 2004.

Asexual reproduction of the new Zonal *Geranium* by vegetative terminal cuttings in a controlled environment in De Lier, The Netherlands, since July, 2004, has shown that the unique features of this new Zonal *Geranium* are stable and reproduced true to type in successive generations.

SUMMARY OF THE INVENTION

The cultivar Fisum Lilac Eye has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Fisum Lilac Eye'. These characteristics in combination distinguish 'Fisum Lilac Eye' as a new and distinct cultivar of Zonal *Geranium:*

1. Upright plant habit.
2. Freely basal branching habit.
3. Dark green-colored leaves.
4. Freely flowering habit.
5. Semi-double red purple-colored flowers with slightly lighter-colored central splotches.
6. Good garden performance.

Plants of the new Zonal *Geranium* differ primarily from plants of the parent selections in plant size and flower color.

Plants of the new Zonal *Geranium* can be compared to plants of the *Pelargonium×hortorum* cultivar Meridonna, disclosed in U.S. Plant Pat. No. 9,152. In side-by-side comparisons conducted in De Lier, The Netherlands, plants of the new Zonal *Geranium* differed from plants of the cultivar Meridonna in the following characteristics:

1. Plants of the new Zonal *Geranium* had more durable leaves than plants of the cultivar Meridonna.
2. Plants of the new Zonal *Geranium* had darker green-colored leaves than plants of the cultivar Meridonna.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately described the colors of the new Zonal *Geranium*. The photograph comprises a side perspective view of a typical flowering plant of 'Fisum Lilac Eye' grown in a container.

DETAILED BOTANICAL DESCRIPTION

The aforementioned photograph and following observations, measurements and values describe plants grown in De Lier, The Netherlands in a glass-covered greenhouse during the winter and early spring and under conditions which closely approximate commercial production. During the production of the plants, day temperatures ranged from 14° C. to 20° C., night temperatures ranged from 8° C. to 18° C. and light levels ranged from 10,000 lux to 50,000 lux. Plants were about three months old when the photographs and the description were taken. In the detailed description, color references are made to The Royal Horticultural Society Colour Chart, 1995 Edition, except where general terms of ordinary dictionary significance are used.

Botanical classification: *Pelargonium×hortorum* cultivar Fisum Lilac Eye.

Parentage:

*Female, or seed, parent.*—Unnamed selection of *Pelargonium×hortorum,* not patented.

*Male or pollen parent.*—Unnamed selection of *Pelargonium×hortorum,* not patented.

Propagation:

*Type.*—By vegetative terminal cuttings.

*Time to initiate roots, summer.*—About five to seven days at temperatures of 22° C.

*Time to initiate roots, winter.*—About five to ten days at temperatures of 22° C.

*Time to produce a rooted young plant, summer.*—About two to three weeks at temperatures of 20° C.

*Time to produce a rooted young plant, winter.*—About two to four weeks at temperatures of 20° C.

*Root description.*—Fine, fibrous.

*Rooting habit.*—Freely branching, moderately dense.

Plant description:

*General appearance.*—Upright plant habit; uniformly mounded; densely foliated.

*Growth and branching habit.*—Moderately vigorous growth habit. Freely basal branching habit with about seven lateral branches developing per plant.

*Plant height, to top of umbels.*—About 15 cm to 25 cm.

*Plant width.*—About 12 cm to 20 cm.

*Lateral branches.*—Length: About 5 cm to 25 cm. Diameter: About 5 mm to 8 mm. Internode length: About 4 mm to 3 cm. Texture: Pubescent. Strength: Strong, sturdy. Color: 144B.

Foliage description:

*Arrangement.*—Alternate; simple.

*Length.*—About 5 cm.

*Width.*—About 7 cm to 8 cm.

*Shape.*—Orbicular.

*Apex.*—Rounded.

*Base.*—Cordate.

*Margin.*—Crenate; slightly undulate.

*Venation pattern.*—Palmate.

*Texture, upper and lower surfaces.*—Densely pubescent.

*Color.*—Developing foliage, upper surface: 141A. Developing foliage, lower surface: 138B. Fully developed, upper surface: Between 139B and 143A; venation, 145A. Fully developed, lower surface: Between 139C and 143A; venation, 145B. Zonation pattern: Not observed.

*Petiole.*—Length: About 3 cm to 7 cm. Diameter: About 2 mm to 3 mm. Texture, upper and lower surfaces: Pubescent. Color, upper and lower surfaces: 143C.

Flower description:

*Flower arrangement.*—Semi-double rotate flowers arranged in rounded hemispherical umbels arising from apical leaf axils. Umbels displayed above the foliage or strong peduncles. Flowers face upright outward. Flowers persistent. Flowers not fragrant.

*Quantity of flowers.*—Freely flowering habit; about 10 to 40 flower buds and open flowers per umbel.

*Flowering season.*—Year-round under greenhouse conditions. In the garden in De Lier, The Netherlands, flowering is continuous from late spring until frost in autumn.

*Flowering longevity.*—Individual flowers last about two to eight days on the plant.

*Umbel height.*—About 7 cm to 10 cm.

*Umbel diameter.*—About 5 cm to 8 cm.

*Flower diameter.*—About 5 cm.

*Flower depth* (*height*).—About 5 cm.

*Flower buds.* —Length: About 5 mm to 7 mm. Diameter: About 5 mm to 6 mm. Shape: Globular to elliptic. Color: 143C.

*Petals.*—Quantity per flower. About five to eight. Length: About 2.6 cm to 2.9 cm. Width: About 2 cm to 3 cm. Shape: Broadly spatulate to obovate. Apex: Rounded. Base: Attenuate. Margin: Entire. Texture, upper and lower surfaces: Smooth, glabrous. Color: When opening, upper surface: 66A; central splotch, 66C. When opening, lower surface: 66A. Fully opened, upper surface: 74A; central splotch, close to 74C; towards the base, 155D; venation, 66A. Fully opened; lower surface: 74B.

*Petaloids.*—Quantity per flower: None to about three. Length: About 1 mm to 2 cm. Width: About 2 mm to 2 cm. Shape: Irregularly shaped; obovate to irregularly oblanceolate. Apex: Rounded. Base: Attenuate. Margin: Entire. Texture, upper and lower surfaces: Smooth, glabrous. Color: When opening, upper and lower surfaces: 66A. Fully opened, upper and lower surfaces: 74B.

*Sepals.*—Quantity per flower: Five, arranged in a single whorl. Length: About 1.1 cm to 1.3 cm. Width: About 2 mm to 4 mm. Shape: Ovate, oblong. Apex: Acute to acuminate. Base: Truncate. Margin: Entire. Texture, upper and lower surfaces: Densely pubescent. Color: Immature, upper and lower surfaces: 143C; towards the margin, 157A. Mature, upper surface: 143A; towards the base, 178B; towards the margin, 157A; venation, 178B. Mature, lower surface: 143A; towards the base, 180B; towards the margin, 157A; venation, 180B.

*Peduncle* (*umbel stem*).—Length: About 9 cm to 16 cm. Diameter: About 4 mm. Strength: Strong. Angle: Erect to about 30° C. from vertical. Texture: Pubescent. Color: 143A.

*Pedicel* (*individual flower stem*).—Length: About 2.5 cm to 3 cm. Diameter: About 1 mm to 2 mm. Strength: Moderately strong. Angle: Erect to about 60° C. from vertical. Texture: Pubescent. Color: 187B.

*Reproductive organs.*—Androecium: Stamen quantity per flower: About one to ten. Filament length: About 4 mm to 8 mm. Filament color: Close to 155A; towards the anther, 61B. Anther length: About 2 mm to 3 mm. Anther shape: Oblong. Anther color: 58C. Pollen amount: Moderate. Pollen color: 171B. Gynoecium: Pistil quantity per flower: One. Pistil length: About 7 mm to 1 cm. Stigma shape: Tapering: reflexed. Stigma color: 74A. Style length: About 3 mm to 4 mm. Style color: 61A. Ovary color: 138C.

*Seed.*—Seed development has not been observed.

Disease/pest resistance: Plants of the new Zonal Geranium have not been observed to be resistant to pathogens and pests common to Zonal Geraniums.

Garden performance: Plants of the new Zonal *Geranium* have been observed to tolerate rain, wind, and temperatures ranging from about 0° C. to about 40° C. and have demonstrated good garden performance.

It is claimed:

1. A new and distinct Zonal *Geranium* plant named 'Fisum Lilac Eye' as illustrated and described.

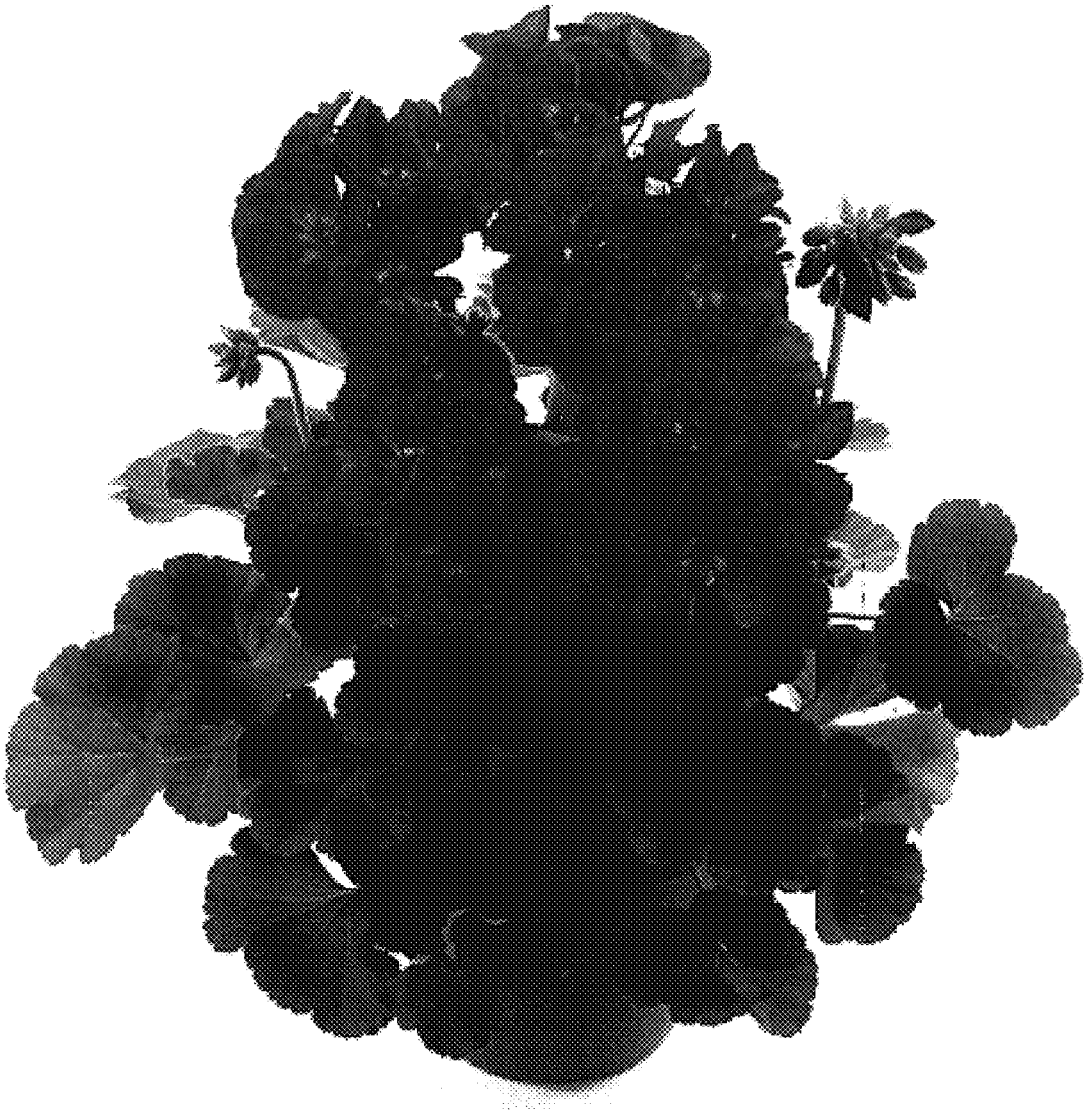

* * * * *